United States Patent [19]

Plessis et al.

[11] Patent Number: 4,731,807
[45] Date of Patent: Mar. 15, 1988

[54] X-RAY EXAMINATION APPARATUS

[75] Inventors: André Plessis, Clamart; Emile Gabbay, Paris; Jacques Trotel, Palaiseau, all of France

[73] Assignee: Thomson-CGR, Paris, France

[21] Appl. No.: 913,126

[22] Filed: Sep. 29, 1986

[30] Foreign Application Priority Data

Oct. 8, 1985 [FR] France ................ 85 14885

[51] Int. Cl.[4] .......................... G21K 5/10; G21K 3/00
[52] U.S. Cl. .................................. 378/156; 378/147; 378/146; 378/157
[58] Field of Search ............... 378/159, 156, 157, 146, 378/147, 148, 149, 150, 82, 85, 5, 49, 12, 113, 137, 158

[56] References Cited

U.S. PATENT DOCUMENTS

| 4,020,356 | 4/1977 | Brahme | 378/149 |
| 4,149,081 | 4/1979 | Seppi | 378/99 |
| 4,177,382 | 12/1979 | Hounsfield | 378/99 |
| 4,255,664 | 3/1981 | Rutt | 378/5 |

FOREIGN PATENT DOCUMENTS 2950780 11/1979 Fed. Rep. of Germany .
8201124 4/1987 PCT Int'l Appl. .

Primary Examiner—Carolyn E. Fields
Assistant Examiner—Joseph A. Hynds
Attorney, Agent, or Firm—Roland Plottel

[57] ABSTRACT

The present invention concerns an X-ray examination apparatus allowing to produce images of an object through the scanning of the object by at least two fan-shaped beams having different energy spectra, and obtained from a single X-ray source, thereby allowing to obtain simultaneously images of the object adapted to contain different informations.

11 Claims, 2 Drawing Figures

U.S. Patent     Mar. 15, 1988     4,731,807
FIG_1
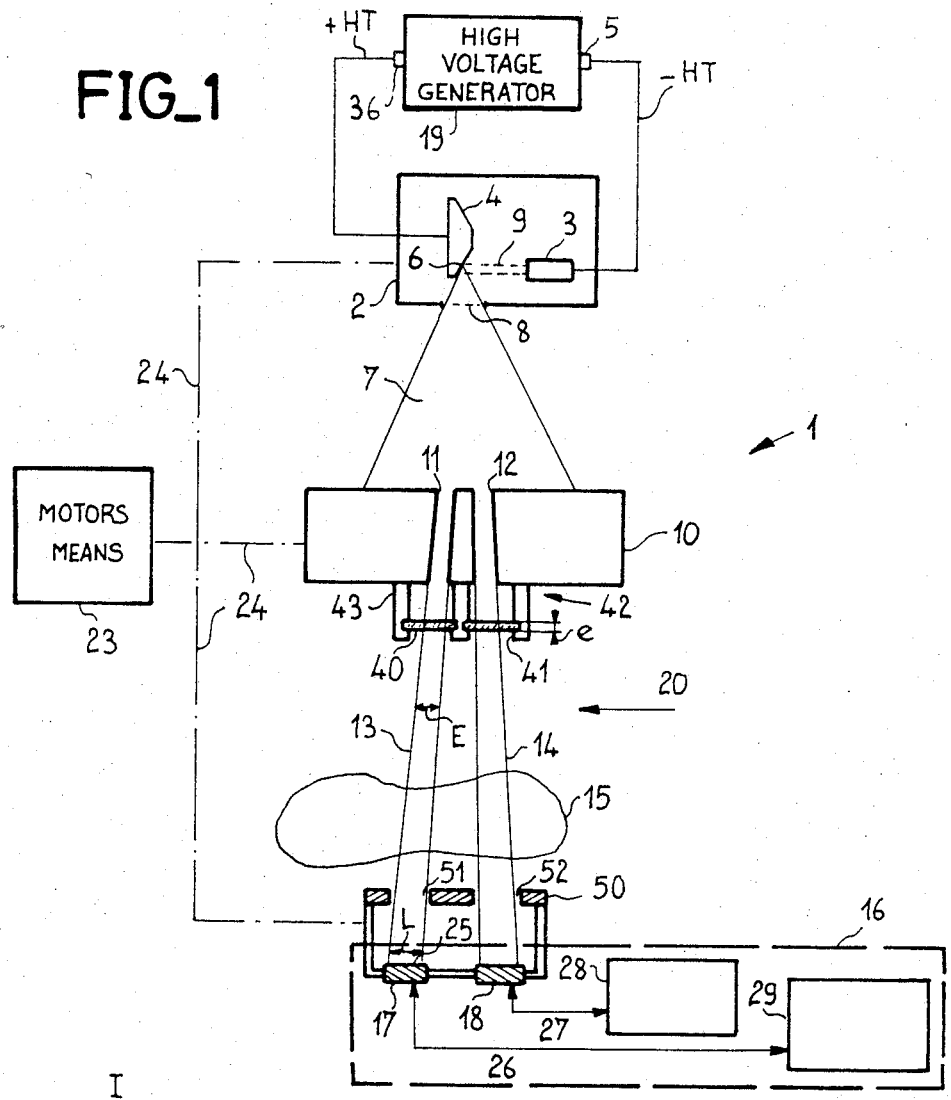
FIG_2
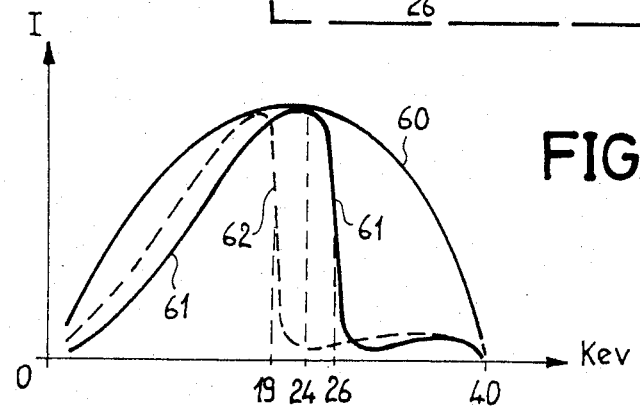

X-RAY EXAMINATION APPARATUS

BACKGROUND OF THE INVENTION

The present invention relates to an X-ray examination apparatus of the type in which an image of an object is formed through scanning the object by a fan-shaped flat X-ray beam.

One particular advantage in the use of a fan-shaped beam, collimated with respect to the receiver, lies in a considerable decrease of the X-ray diffused by the object itself and thus in an improvement of the quality of the image, only a relatively thin segment or slice of the object to be examined being crossed through by the X-ray beam at each instant.

Images in traditional radiology practices, in certain cases, present difficulty in reading; they do not contain sufficiently accurate informations to perform a reliable diagnosis, especially when the examination concerns body tissues presenting only slight differences of absorption to the X-ray, such as aqueous tissues and adipous tissues, or concern search of bodies in low concentration condition.

U.S. Pat. No. 3,515,874 describes a radiography apparatus producing a substantially monochromatic X-ray beam in order to increase on a negative the contrast presented between certain elements having only slight differences of absorption. This apparatus comprises more particularly a physical filter the nature of which allows, in relation to the energy of the incident electron beam, to obtain an X-ray beam having a spectrum that is reduced in energy or wavelengths, containing the wavelength at which is located an absorption discontinuity characteristic of the physical filter.

This constitutes a considerable improvement, but which in many cases is still insufficient, for example, when it is desired to study, in vascular, very fine vessels concealed in a highly diffusing medium.

The idea upon which the applicant has based the present invention, was that in such cases, several perfectly superimposable images of the same area and comprising different informations would allow to display the presence of these vessels.

SUMMARY OF THE INVENTION

The present invention relates to an X-ray examination apparatus allowing to produce, simultaneously, several negatives or exposures of a single area or zone, each containing different informations or data, these differences being in particular related to a differential absorption phenomenon of two spectrum of X-ray of different wavelength; the simultaneity of making the exposures allows a perfect superposition of these exposures.

According to the invention, an X-ray examination apparatus comprising a tube producing X-ray, collimation means defining from the said X-ray a fan-shaped flat beam, means for performing a scanning of an object to be examined by the said fan-shaped beam, means for receiving the X-ray, is characterized in that the said collimation means define from the said X-ray at least one second flat fan-shaped beam scanning the said object according to the same movement as the first fan-shaped beam, and wherein the said X-ray examination apparatus comprises furthermore means for conferring upon the first and second fan-shaped beam different energy radiation spectra, prior to their crossing through the object to be examined, in order to perform simultaneously at least two images of the said object adapted to contain different informations.

BRIEF DESCRIPTION OF THE DRAWINGS

The present invention will become more apparent from the following description, given by way of non-limitative example, with reference to the appended drawings in which:

FIG. 1 shows schematically an X-ray examination apparatus according to the invention;

FIG. 2 is a graph representing energy radiation spectra conferred upon the X-ray beams by the means according to the invention.

DETAILED DESCRIPTION OF THE INVENTION

FIG. 1 represents schematically an examination apparatus 1. The examination apparatus 1 comprises an X-ray emitting tube 2 of a classical type comprising a cathode 3 and an anode 4 of the rotating anode type, for example; the cathode 3 and the anode 4 being respectively connected to a negative output 5 and to a positive output 36 of a high voltage generator 19 supplying the high voltage power supply HT of the X-ray emitting tube 2.

During operation, the cathode 3 generates electrons that are accelerated under the effect of the high voltage HT and form an electron beam 9 that bombards the anode 4, at a point constituting a focus 6 and the X-ray source 7.

The X-ray issues from the X-ray emitting tube through an output window or slot 8, for example in a conical form, prior to encountering collimation means 10.

According to one characteristic of the invention, at least two separated beams are produced from the X-ray.

In the example described, the collimation means 10 comprise several openings or passages 11, 12 through which pass a friction of the X-ray; the number of these passages 11, 12 being limited to two in the non-limitative example described. The form of each passage 11, 12 is adapted in a manner itself known per se, so that the X-ray issuing from each of these passages 11, 12 has the form of a flat fan-shaped beam respectively 13, 14; the fan-shaped beams 13, 14 being represented on FIG. 1 according to their thickness E, the planes of the fan of these beams extending in planes perpendicular to that of the figure, each fan having as its apex the focus 6.

It is thus possible to simultaneously produce a first and a second fan-shaped beam 13, 14 intended to expose one after the other the same areas of an object 15, in order to obtain in a manner practically simultaneous two images of this object 15; these images being obtained by means 16 for receiving the X-ray represented in a frame in dotted lines.

In the non-limitative example described, the receiving means 16 comprise two detecting devices formed by a first and a second detecting strip 17, 18 exposed respectively by the first and the second beams 13, 14 of which they follow the scanning movement of the object 15.

The scanning movement, in itself classical, is performed for example along a mean direction 20 substantially perpendicular to the fan of the beams 13, 14 due to means for performing the scanning which are in themselves known; these means can comprise for example actuating means 23, connected to mechanicals means 24 (symbolized on the figure by connections in dotted lines) in order to connect the X-ray emitting tube 2, the collimation means 10 and the detecting strips 17, 18.

The scanning movement can consist of a translation movement, with respect to the object 15, of the assembly formed by the X-ray emitting tube 2, the collimation means 10 and the detecting strips 17, 18 or by any other movement that allows scanning of the object 15 by at least two flat fan-shaped beans 13, 14 disposed one behind the other in the mean direction 20 of this movement, such as in the example described.

The detecting strips 17, 18 are constituted in a manner know per se, by a plurality of detectors (not represented) sensitive to X-rays, disposed in such a way as to form an input plane 25 of which the width L is represented in the plane of the figure, and of which the length (non-visible) extends in a plane perpendicular to that of the figure parallel to the plane of the fan-shape of the beams 13, 14.

Each detecting strip 17, 18 is connected by electrical links 26, 27 to a processing unit 29, 28 in order to transfer during the scanning movement, in a classical manner known per se, signals supplied by each detector and corresponding to the quantity received, and from which each processing unit 29, 28 produces at the end of the scanning, an image of the object 15. The two processing units 29, 28 being independent from each other, it is also possible to obtain two complete images (not represented) of the object 15: from the first beam 13, the first image is obtained by the first detecting strip 17 and the first processing unit 29 which forms a first receiving assembly 17, 29; from the second beam 14, the second image is obtained by the second detecting strip 18 and the second processing unit 28 which forms a second receiving assembly 18, 28. The two images can be displayed by the display device(s) (not represented and known per se); but the two receiving assemblies 17, 29 - 18, 28 can be of a different type, such as the type comprising for example a radiographic film.

According to one main characteristic of the invention, the X-ray examination apparatus according to the invention comprises means for conferring upon the beams 13, 14 different energy radiation spectra.

These means are constituted by at least one physical filter 40, 41 interposed on the path of one of the X-ray beams 13, 14 prior to said beams having crossed through the object 15.

In the non-limitative example of the description, a first and a second physical filter 40, 41 are respectively interposed on the path of the first and of the second beams 13, 14 and are disposed at an output 42 of the collimation means 10 to which they are secured by brackets 43.

Each physical filter 40, 41 is made of a thin sheet of an element or an alloy of which, on the one hand the atomic number and, on the other hand the thickness e are selected in function of the effect that it is desired to obtain upon the X-ray radiation spectrum 7 issuing from the focus 6.

It is known that the absorption coefficient relative to a determined element remains invariable within very wide wavelength bands, but presents very sudden variations for certain value ranges about the absorption wavelengths $\lambda K$, $\lambda L$, $\lambda M$ relative to the element involved.

This particular is employed in the invention, under conditions allowing each physical filter 40, 41 to be opaque for the greatest part of the spectrum, and to be transparent for a small part of this spectrum; the material filters 40, 41 being produced from materials made of different natures, the wavelength or energy ranges for which they present low absorption are different.

The beams 13, 14 having different energy spectra, they are carriers, after having crossed through the object 15, of different informations resulting from the differential absorption phenomena mentioned hereinabove, produced at different wavelengths for each beam 13, 14 which can thus improve the image of certain bodies.

With the purpose of improving the quality of the images, the X-ray examination apparatus 1 according to the invention comprises moreover means for preventing that the X-ray (non represented) diffused by the object 15 itself and generated by one or other of the beams 13, 14, the first beam 13 for example, be perceived by the second detecting strip 18 corresponding to the second beam 14.

With this aim, in the non-limitative example described, the examination device 1 comprises between the detecting strips 17, 18 and the object 15, a plate 50 absorbing X-ray, and comprising slots 51, 52 disposed respectively opposite the first and the second detecting strip 17, 18; the plate 50 being made integral with the detecting strips 17, 18 with which it is displaced during the scanning movement.

FIG. 2 represents several energy radiation spectra obtained according to the invention, from a high voltage, for example, of 40 kV, and from an anode in tungsten; the energy in keV being brought to the abscissae and the intensities I in ordinates.

A first curve 60 represents the X-ray energy radiation spectrum 7, prior to interposition of the physical filters 40, 41; the intensity increases from zero to reach a maximum towards about 24,25 keV, and decreases thereafter until it is cancelled out at 40 keV.

The curve 61 represents the spectrum conferred upon one of the fan-shaped beams, the first beam 13 for example after interposition of the first physical filter 40 made of silver for example, its intensity increases from zero much more slowly than the first curve 60 and reaches a maximum towards 26 keV from which it suddenly decreases to a value of almost zero.

A third curve 62, shown in dotted lines for enhanced clarity, represents the spectrum of the second beam 14, after interposition of the second material filter 41 made for example of molybdenum; the intensity there again increases from zero much more slowly than the first curve 60, and reaches a maximum towards 19 keV at which point it decreases suddenly.

The sudden decreases in intensity at 26 and 19 keV, shown by the second and third curves 61, 62 are due respectively to the absorption discontinuity presented by the silver and the molybdenum and represent respectively a limit of the energy spectrum of the first and of the second beams 13, 14.

The relatively slow increase prior to these maximum intensities at 26 keV and 19 keV, are particularly associated to the thickness e (shown in FIG. 1) of the materials from which are formed the physical filters 40, 41; this thickness e being, in the non-limitative example of the description, from about 0.03 mm to 0.05 mm.

We claim:

1. An X-ray examination apparatus comprising an X-ray tube producing X-rays, collimation means defining a first and a second separated fan-shaped flat beams of said X-rays, means for scanning an object by said first and second fan-shaped beams along a mean direction substantially perpendicular to the planes of said first and second fan-shaped flat beams, receiving means sensitive to the X-rays, means for conferring to each said first and second beams a different energy radiation spectra prior to their crossing through the object to be examined, and wherein the receiving means comprise a first and a second receiving assemblies each forming a shadow image of the object respectively from the first and the second fan-shaped flat beam in order to simultaneously obtain at least two images of the object.

2. X-ray examination apparatus according to claim 1, wherein said means for conferring upon the first and second beams different energy spectra, comprise at least one physical filter having a thickness disposed on the path of the one or the other of said first and second beams.

3. X-ray examination apparatus according to claim 1, wherein said means for conferring upon said beams different spectra comprise a first and a second physical filter having thickness and of different X-ray properties, and disposed respectively on the path of the first and second beams prior to said beams crossing through the said object.

4. X-ray examination apparatus according to claim 1, wherein said first and second receiving assemblies comprise respectively a first and a second detecting strip exposed respectively by said first and second beams and each connected to a processing unit.

5. X-ray examination apparatus according to claim 4, wherein said first and second detecting strips are displaced during a scanning movement synchronized with said first and second beams.

6. X-ray examination apparatus according to claim 4 further comprising means for absorbing X-rays.

7. X-ray examination apparatus according to claim 6, wherein said means for absorbing the diffused X-rays are constituted by a plate disposed between said object and said first and second detecting strips and comprising a first and a second slot located facing said detecting strips.

8. X-ray examination apparatus according to claim 7, wherein said plate is made integral with the detecting strips.

9. X-ray examination apparatus according to claim 2, wherein said physical filters are disposed at an exit of the collimation means.

10. X-ray examination apparatus according to claim 2, wherein each physical filter is constituted from a material of which an absorption discontinuity is located at a wavelength corresponding to an energy limit conferred to the radiation spectra of said beams.

11. X-ray examination apparatus according to claim 2, wherein the intensity of the radiation spectrum of said beams is limited at low energies by the thickness of said physical filters.

* * * * *